(12) United States Patent
Everett

(10) Patent No.: US 7,160,717 B2
(45) Date of Patent: Jan. 9, 2007

(54) LED ARRAY FOR ILLUMINATING CELL WELL PLATES AND AUTOMATED RACK SYSTEM FOR HANDLING THE SAME

(75) Inventor: Keith Everett, Raleigh, NC (US)

(73) Assignee: Biolex, Inc., Pittsboro, NC (US)

( * ) Notice: Subject to any disclaimer, the term of this patent is extended or adjusted under 35 U.S.C. 154(b) by 37 days.

(21) Appl. No.: 10/725,044

(22) Filed: Dec. 1, 2003

(65) Prior Publication Data
US 2004/0110279 A1 Jun. 10, 2004

Related U.S. Application Data

(63) Continuation of application No. 10/080,918, filed on Feb. 22, 2002, now Pat. No. 6,680,200.

(51) Int. Cl.
*C12M 1/36* (2006.01)
(52) U.S. Cl. .............................. 435/286.2; 435/288.4; 435/289.1; 435/292.1; 435/305.2; 47/58.1 LS; 47/58.1 SE; 47/DIG. 8
(58) Field of Classification Search ........... 47/58.1 LS, 47/58.1 SE, DIG. 6; 435/284.1, 288.4, 305.2, 435/289.1, 292.1, 286.2
See application file for complete search history.

(56) References Cited

U.S. PATENT DOCUMENTS

| | | | |
|---|---|---|---|
| 3,233,146 A | 2/1966 | Vacha | |
| 3,514,668 A | 5/1970 | Johnson et al. | |
| 3,529,379 A | 9/1970 | Ware | |
| 3,876,907 A | 4/1975 | Widmayer | |
| 3,898,643 A | 8/1975 | Ettlinger | |
| 3,905,153 A | 9/1975 | Enter | |
| 3,930,335 A | 1/1976 | Widmayer | |
| 3,931,695 A | 1/1976 | Widmayer | |
| 4,037,148 A | 7/1977 | Owens et al. | |
| 4,084,905 A | 4/1978 | Schreiber et al. | |
| 4,146,993 A | 4/1979 | Freeman, Sr. | |
| 4,156,166 A | 5/1979 | Shapiro et al. | |
| 4,255,897 A | 3/1981 | Ruthner | |
| 4,396,872 A | 8/1983 | Nutter | |
| 4,626,065 A | 12/1986 | Mori | |
| 4,650,336 A | 3/1987 | Moll | |
| 4,724,633 A | 2/1988 | Kadkade | |
| 4,732,443 A | 3/1988 | Mori | |
| 4,749,916 A | 6/1988 | Yamazaki et al. | |
| 4,768,390 A | 9/1988 | Baker et al. | |
| 4,914,858 A | 4/1990 | Nijssen et al. | |
| 5,012,609 A | 5/1991 | Ignatius et al. | |
| 5,111,612 A | 5/1992 | Takishima et al. | |
| 6,150,158 A | 11/2000 | Bhide et al. | |

U.S. PATENT DOCUMENTS

| | | | |
|---|---|---|---|
| 6,554,450 B1 * | 4/2003 | Fang et al. ................. | 362/231 |
| 6,680,200 B1 * | 1/2004 | Everett ....................... | 435/420 |
| 2003/0009933 A1 | 1/2003 | Yoneda et al. | |

\* cited by examiner

*Primary Examiner*—David Redding
(74) *Attorney, Agent, or Firm*—Alston & Bird LLP

(57) ABSTRACT

An assembly for promoting the growth of plant tissues that includes a plurality of plates each defining an array of wells wherein each of the wells contains a tissue sample. Support for the plates is provided by a rack having a plurality of vertically stacked shelves that may include one or more register depressions that urge the plates into predetermined positions. Light for the tissue samples is provided by a plurality of light-emitting diode arrays each mounted on a circuit board. Each circuit board is supported by a respective card edge connector of the rack so that the light-emitting diodes are in proximity to the plates supported on one of the shelves therebelow. Preferably, the light-emitting diode array corresponds to the well array supported in the registered position on the shelf therebelow so that each light-emitting diode is centered above a respective one of the wells.

20 Claims, 6 Drawing Sheets

US 7,160,717 B2

LED ARRAY FOR ILLUMINATING CELL WELL PLATES AND AUTOMATED RACK SYSTEM FOR HANDLING THE SAME

CROSS-REFERENCE TO RELATED APPLICATIONS

This application is a Continuation of U.S. application Ser. No. 10/080,918 filed Feb. 22, 2002 now U.S. Pat. No. 6,680,200, which is hereby incorporated herein in its entirety by reference.

FIELD OF THE INVENTION

The present invention is related to the use of artificial lighting systems to promote plant growth, and more particularly, to the use of lighting systems to promote growth of plant tissue in cell well plates.

BACKGROUND OF THE INVENTION

In biological and biochemical screening systems that employ plant tissue, it is important that the growth of the plant tissue be promoted. Growth of the plant tissue is affected by several factors which include the amount and type of nutrients supplied to the tissue, the physical support provided for the tissue, the temperature of the tissue environment and the amount of light delivered to the plant tissue. With respect to the availability of light, most screening systems employ artificial light which can be controlled and is not subject to the vagaries of the weather. In addition, the screening systems typically employ plates wherein each plate defines multiple wells. Each of the wells holds and isolates a separate tissue sample so as to avoid contamination with other tissue samples and the environment.

Existing systems for promoting plant tissue growth typically employ a rack, or "hotel," having multiple shelves each holding a plurality of the multiple well plates. Above each shelf is a bank of incandescent or fluorescent lights providing illumination to the multi-well plates and the tissue contained therein. The rack however, has a limited vertical stacking capacity as the lights must be kept a safe distance from the plant tissue to avoid excessive build-up of heat and because the incandescent and fluorescent lights are relatively bulky. Each shelf and light bank combination requires about one foot of vertical space, limiting a normal room with eight feet high ceilings to seven or eight shelves. In addition, incandescent or fluorescent lights are not very energy efficient, requiring about 4.4 watts of power per multiple well plate. Such large space and power requirements, coupled with cost constraints, tend to limit the density of the rack and the throughput of plant tissue screening systems.

Therefore, it would be advantageous to have a system for promoting the growth of plant tissues that can supply sufficient light to plant tissue in multiple well plates while also allowing for an increase in throughput of the screening operation. In particular, it would be advantageous to have a system for promoting the growth of plant tissues that does not occupy an excessive amount of space, nor require the use of large amounts of power per plate.

BRIEF SUMMARY OF THE INVENTION

The present invention addresses the above needs and achieves other advantages by providing an assembly for promoting the growth of tissues requiring light to support proliferation. The assembly includes a plurality of plates each defining an array of wells wherein each of the wells contains one of the tissue samples and isolates its tissue sample from the other tissue samples. Support for the plates is provided by a rack having a plurality of vertically stacked shelves spaced a relatively short distance away from each other. Each of the shelves may include one or more register depressions that urge the plates resting thereon into predetermined positions. Light for the tissue samples is provided by a plurality of light-emitting diode arrays wherein each array is mounted on a circuit board. In turn, each circuit board is supported by a respective card edge connector of the rack so that the light-emitting diodes are in proximity to the plates supported on one of the shelves therebelow. Preferably, the light-emitting diode array corresponds to the well array supported in the registered position on the shelf therebelow so that each light-emitting diode is centered above a respective one of the wells.

In one embodiment, the present invention includes an assembly for promoting the growth of tissue samples requiring light to support proliferation. The assembly includes a plate defining therein a plurality of wells arranged in a well array. Each of the plurality of wells is configured to support and isolate one of the tissue samples. Further, the assembly includes a plurality of light-emitting diodes arranged in a light-emitting diode array. The light-emitting diode array corresponds to the well array such that each of the light-emitting diodes is positioned in proximity to a respective one of the wells so as to shine light into the respective one of the wells. Shining of light into the wells promotes proliferation of the tissue supported in the wells. Preferably, each of the light-emitting diodes is centered above its respective one of the wells. Further preferably, each of the light-emitting diodes emits a white light and is an inch or less from the tissue sample in its respective one of the wells.

In another embodiment of the present invention, a plurality plates and light-emitting diode arrays may be supported by a high-density rack. The rack includes a plurality of shelves vertically spaced from each other wherein each of the shelves is configured to support at least one of the plurality of plates. Each of the light-emitting diode arrays is supported by the rack above a respective one of the shelves. Light from the light-emitting diodes shines into the wells of the plate supported on the shelf below so as to promote tissue growth of the samples contained in the plate.

Preferably, each of the light-emitting diode arrays supported by the rack corresponds to the well array of the plate supported therebelow such that each of the light-emitting diodes is positioned above a respective one of the wells. In addition, the shelves of the rack can include register depressions which urge the plates disposed thereon into predetermined positions such that each of the light-emitting diodes is centered above its respective one of the wells. The rack may also include a plurality of card edge connectors that are each configured to receive a circuit board in which the light-emitting diodes are embedded to form a light-emitting diode array. The card edge connectors are positioned to support the circuit boards, and the light-emitting diodes embedded therein, above the shelves supporting the plates. Preferably, the shelves are less than two inches apart allowing a relatively high density of plates to be held by a rack even when vertical storage space is limited.

In yet another embodiment, the high-density rack may be employed with a robotic manipulation system for use in high-throughput screening. The robotic manipulation system includes a plate manipulator that has a range of motion. The rack is positioned so that the plates supported thereon are within the range of motion of the plate manipulator. The plate manipulator is then capable of supporting and removing each plate from the rack for automated processing, such as in a high-throughput sequencing operation.

The present invention has several advantages. The use of light-emitting diodes that are less bulky and emit less heat than fluorescent and incandescent bulbs allows the shelves of the rack to be more closely stacked. More closely stacked shelves increases storage efficiency by reducing the amount of space needed to house an adequate supply of tissue samples. This is particularly important in high-throughput screening operations where thousands of samples are needed on a daily basis. In addition, more plates are accessible to automated plate manipulators, such as robotic arms, that have a limited range of motion. Matching and alignment of each of the wells with its own light-emitting diode allows for calibration of the light beam spread and intensity for optimal tissue growth. Further, the light emitting diodes use light more efficiently and have lower power requirements for promoting tissue growth than fluorescent and incandescent bulbs, averaging about 1.3 watts per standard 4 by 6 plate compared to 4.4 watts for fluorescent and incandescent systems.

BRIEF DESCRIPTION OF THE SEVERAL VIEWS OF THE DRAWINGS

Figure 1:
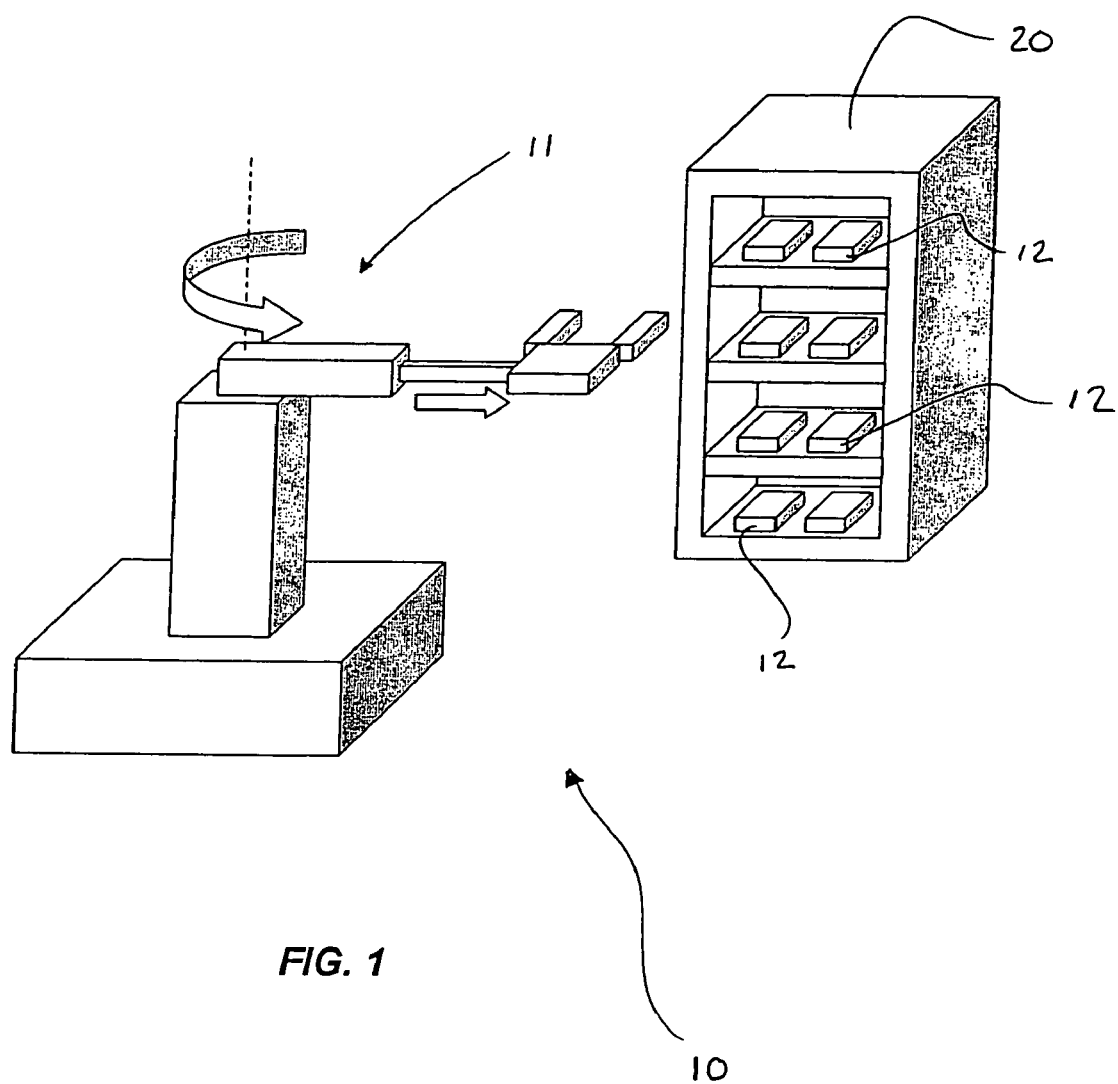
Figure 2:
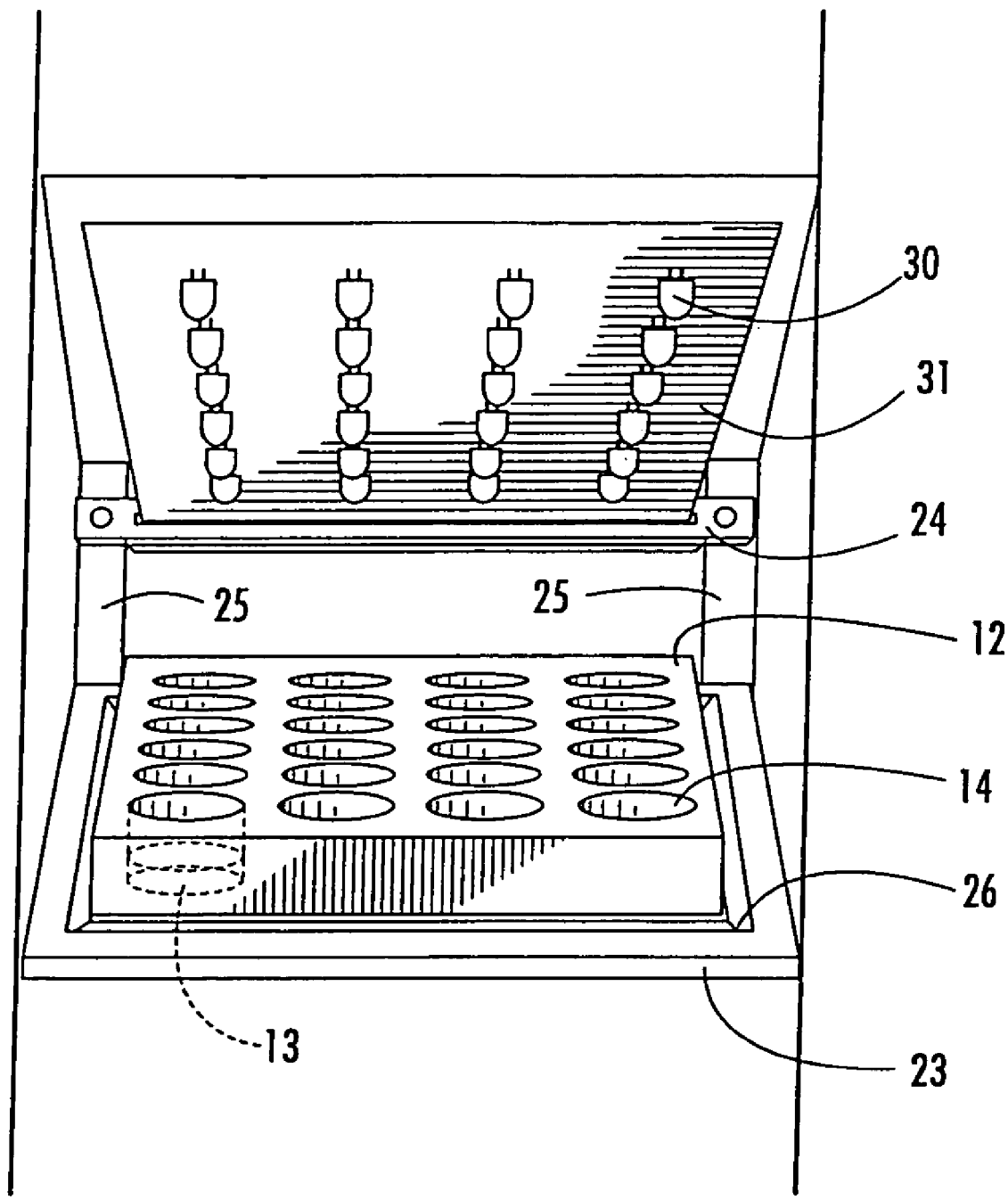
Figure 3:
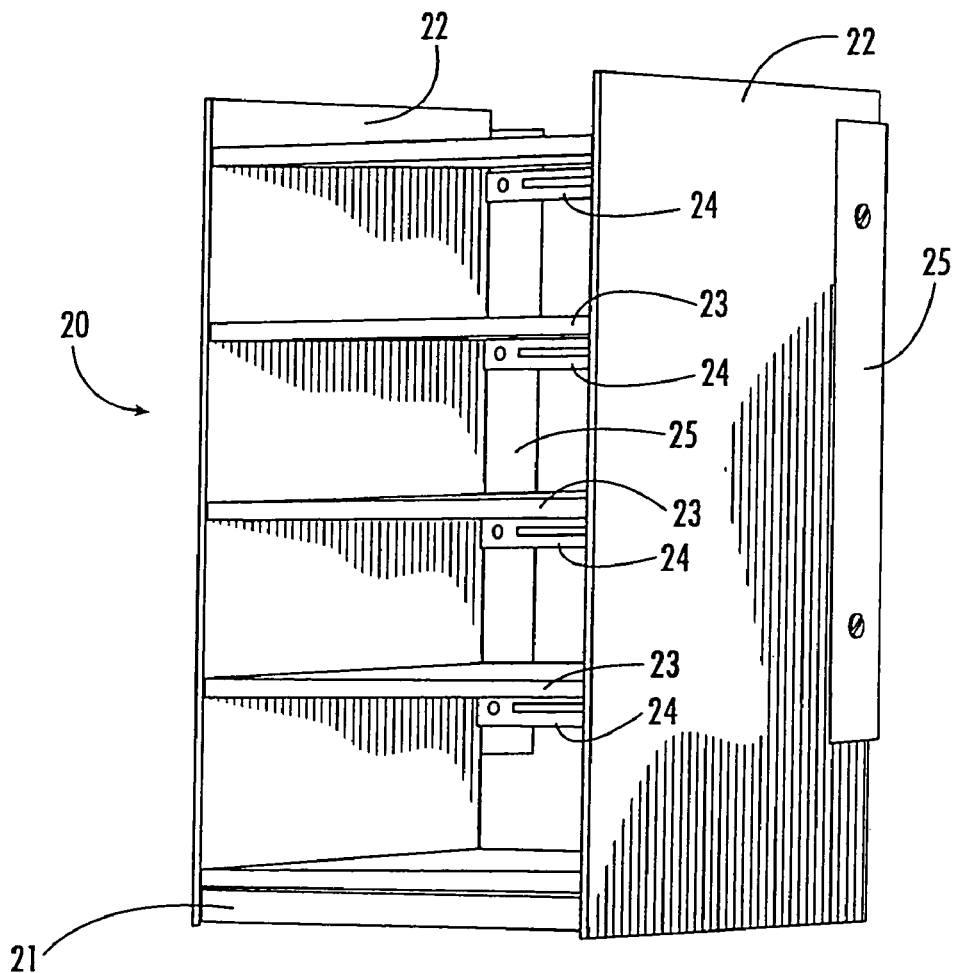
Figure 6:
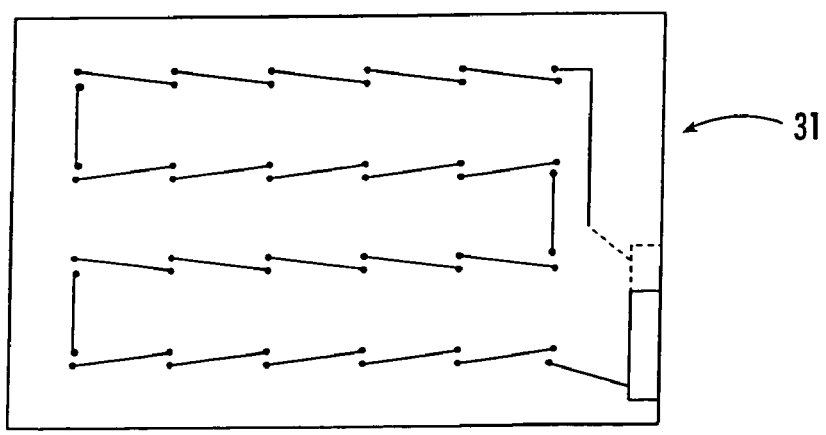
Figure 4:
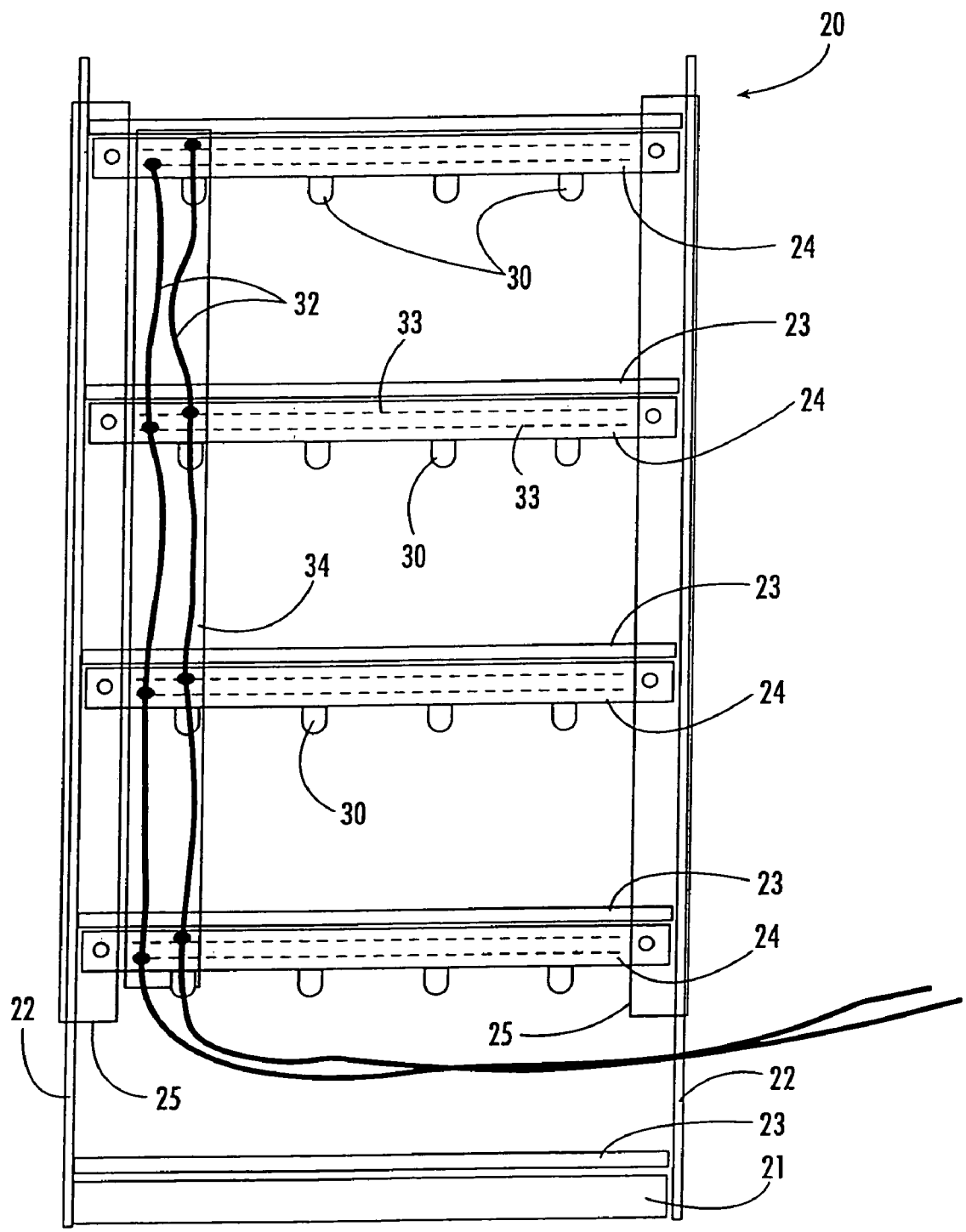
Figure 5:
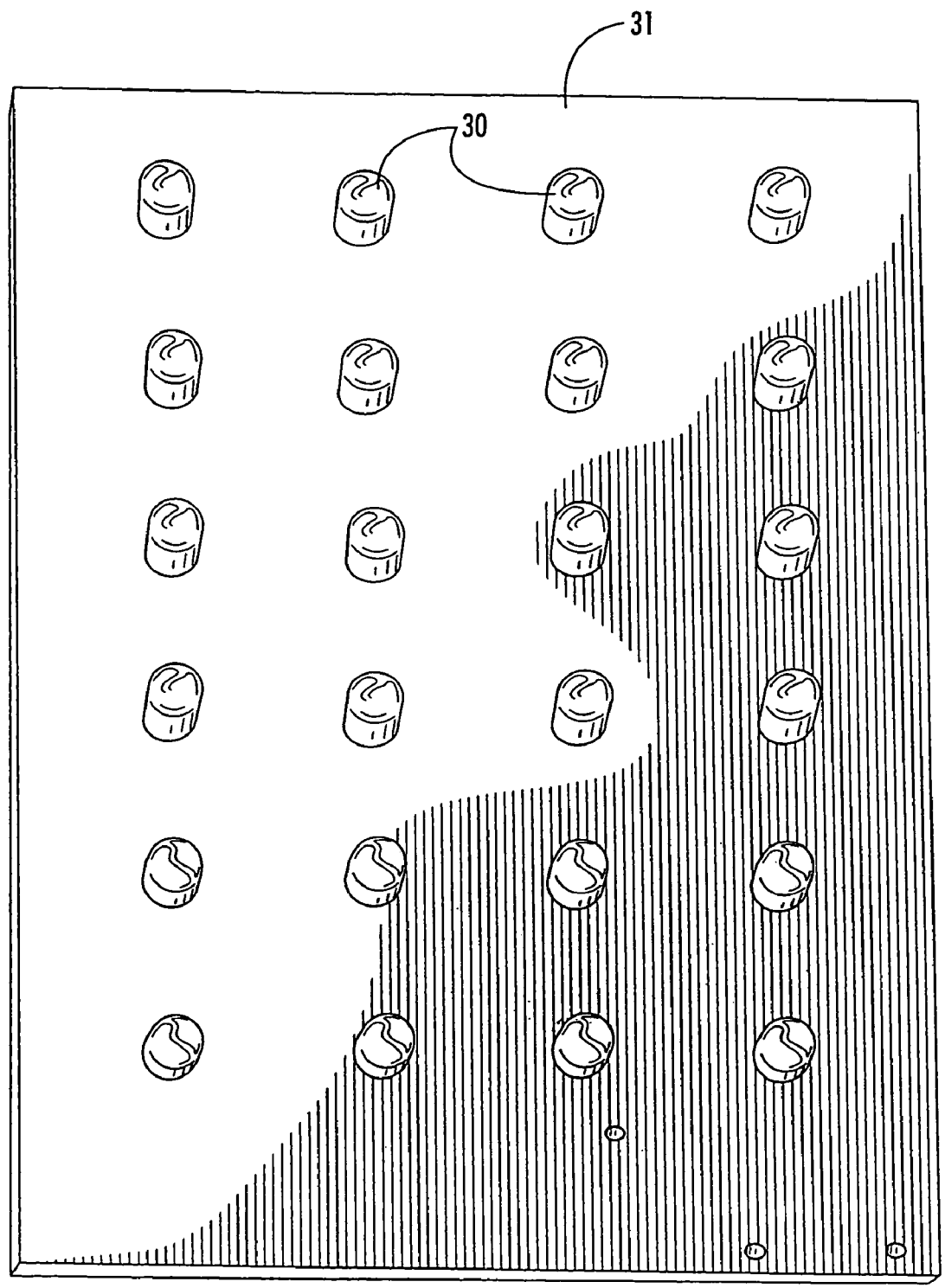
Figure 7:
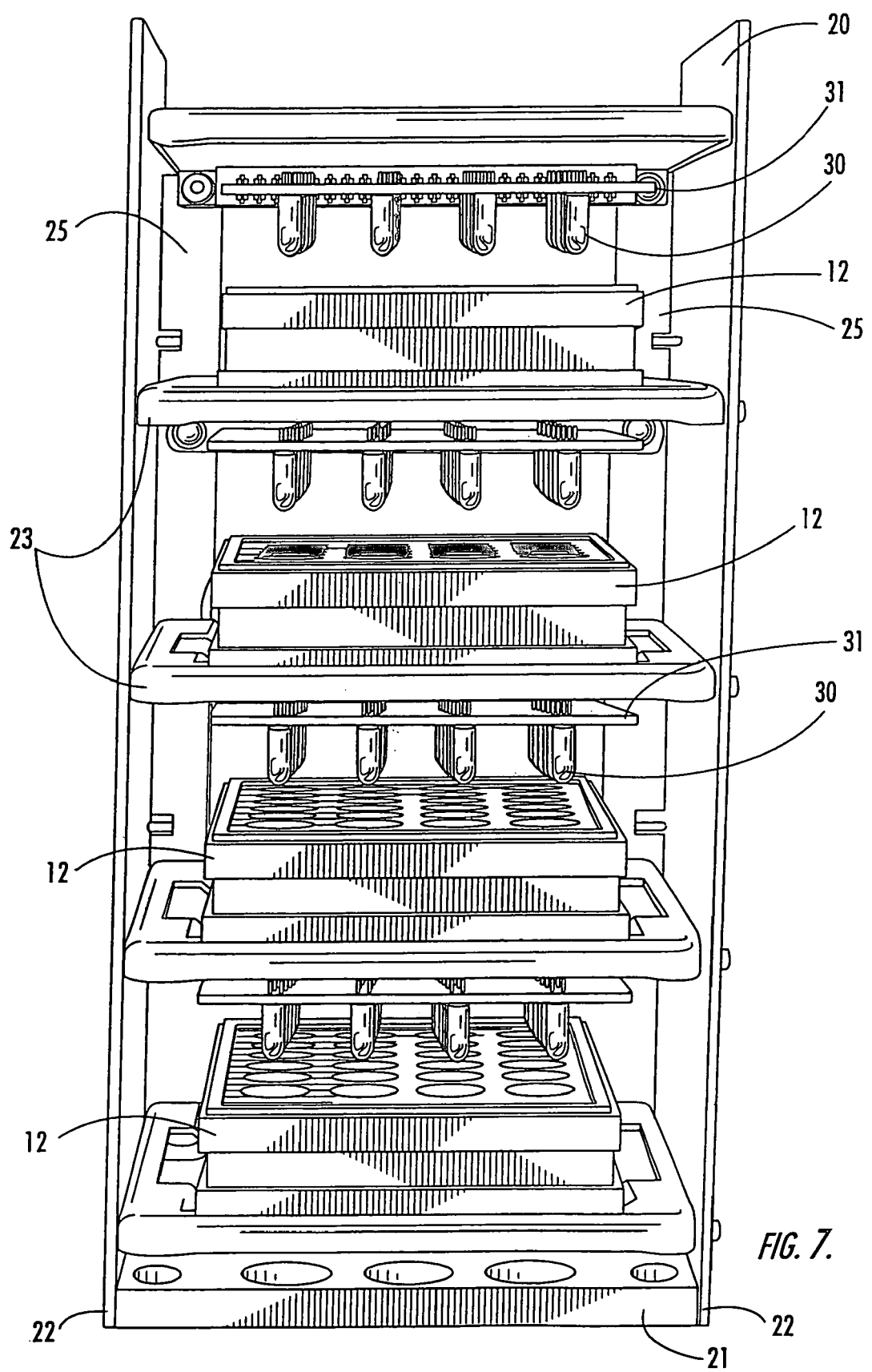

Having thus described the invention in general terms, reference will now be made to the accompanying drawings, which are not necessarily drawn to scale, and wherein:

FIG. 1 is a perspective view of a high throughput screening system of one embodiment of the present invention;

FIG. 2 is a perspective view of a multiple well plate supported and centered below a light-emitting diode array of another embodiment of the present invention;

FIG. 3 is perspective view of the rack shown in FIG. 1 including a plurality of vertically spaced shelves and card edge connectors for supporting a plurality of the well plates and light-emitting diode arrays, respectively, shown in FIG. 2;

FIG. 4 is a rear elevation view of the rack of FIG. 3;

FIG. 5 is a perspective view of the light-emitting diode array of FIG. 2;

FIG. 6 is a bottom plan view of the light-emitting diode array of FIG. 2 including a circuit board for supporting light-emitting diodes; and FIG. 7 is a perspective view of the rack of FIG. 3 with the light-emitting diode arrays and multiple well plates of FIG. 2 installed therein.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

In one embodiment, the present invention comprises a high throughput screening system 10 which includes a robotic system 11 for the automated manipulation of multiple well plates 12 housed in a high-density rack or hotel 20 wherein each of the multiple well plates contains a plurality of plant tissue samples 13, as shown in FIGS. 1 and 2. Above each of the well plates is an array of light emitting diodes (LED's) 30 supported by a circuit board or card 31 that supply light to the plant tissue samples 13 in the wells 14 defined in the well plates 12.

The high-density rack 20 includes a rectangular base 21, a pair of side walls 22, a plurality of shelves 23, a plurality of card edge connectors 24 and a pair of connector supports 25, as shown in FIG. 3. The pair of side walls 22 are horizontally spaced apart across the rectangular base 21. More particularly, the side walls 22 are attached to, and extend vertically upwards from, the left and right sides of the rectangular base 21. The shelves 23 are spaced from each other in the vertical direction and extend between the side walls 22. The pair of side walls are attached to the shelves so as to support the left and right edges of each of the shelves 23. Preferably, the shelves 23 are about 2 inches apart, allowing more than 40 shelves to be stacked in a room with a ceiling height of about 8 feet. In addition, each of the shelves preferably defines at least one depression 26, ledge, edge or other mechanical or electrical device (such as a magnetic field) that urges one of the plates 12 resting thereon into a registered position known by the robotic system 11 for later retrieval and manipulation, as shown in FIG. 2. The rack 20 of the present invention should not be considered limited to the aforedescribed embodiment. The rack could include any structure or assembly that provides supporting surfaces or supports at various orientations and densities for a desired number of the plates 12 or trays holding the plates. Preferably, however, the supporting surfaces should have sufficient clearance for access by the robotic manipulator 11, and some register device for urging the plates 12 into alignment with the corresponding array of LED's 30 and into a position known to the robot for later retrieval.

The connector supports 25 each have an L-angle shape with one leg affixed to a respective one of the side walls 22 and the other leg extending inwards toward the other one of the side walls and along the back of the rack 20, as shown in FIG. 4. The card edge connectors 24 are each mounted to the connector supports 25 above a respective one of the shelves 23, and subjacent the next consecutive one of the shelves in the vertical direction. The card edge connectors 24 each define a horizontal slot sized to receive an edge of one of the circuit boards 31. The horizontal slots also ensure that the circuit boards 31, and hence the arrays of LED's 30, are correctly positioned above the shelves 23.

A pair of power leads 32 extend vertically along the backs of the card edge connectors 24. The power leads 32 are electrically coupled to the horizontal slot of each of the connectors by being soldered to adjacent tabs 33 on the backs of the card edge connectors 24. One of the power leads 32 is attached to a tab on the top of the horizontal slot, while the other is attached to a tab on the bottom of the horizontal slot. Each of the circuit boards 31 is energized, sending power to its LED's, by insertion into its respective one of the card edge connectors 24. A protective shield 34 may be mounted over the power leads, extending in a vertical direction along the back of the rack 20, so as to physically protect the soldered connections as well as shield against interference. Although the card edge connectors 24 allow for easy installation and removal of each array of LED's 30, the circuit boards 31 could also be hard wired into the rack 20.

The number, dimensions and locations of the wells 14 in the well plates 12 are tailored to be compatible with preexisting plate handling equipment, such as the robot 11. For instance, the plate preferably has 24 wells in an array of 4 by 6 (as shown in FIG. 2), or 48 wells in an array of 6 by 8 to be compatible with most handling devices. Other well densities could be used such as 6 wells, or 96 wells that are also compatible with conventional devices. However, non-standard well densities could also be used, such as a single well or a 1000 wells. The well plates 12 can also include transparent covers that further isolate the tissue samples 13 enclosed therein while still allowing the transmission of light from the LED's 30 to the tissue samples.

The LED's are preferably high-brightness, white LED's (Nichia Model No. NSPW-500BS available from Alpinetech of Irvine, Calif., USA) that provide sufficient light for tissue growth when the distance from the tissue 13 is less than one inch. The white LED's emit a relatively full spectrum of light frequencies as compared to non-white LED's. Advantageously, the full spectra emission of the white LED's eliminates the problems of matching different LED's having different spectra to the differing light sensitivities of various plant tissues so as to promote growth. In addition, all of the white LED's may be powered by a single power source.

Further preferably, the LED's 30 are in a twin-lead, 5 mm epoxy package and are loaded in series into the printed circuit board 31 in the array, as shown in FIGS. 5 and 6. Alternatively, some or all of the LED's 30 may also be individually wired, allowing individual control of each of the LED's. Each of the circuit boards 31 preferably has a contact at the top and bottom of the board at its connecting edge positioned so as to correspond to the top and bottom tabs of each horizontal slot. As mentioned above, the LED's need not be supported by a printed circuit board, but could be hardwired into the desired array configurations and positions necessary to shine sufficient light onto the well plates 12.

Preferably, the LED's 30 are spaced in each array so as to correspond to the spacing of the wells 14 defined in each of the cell well plates 12. As a result, each of the LED's 30 are centered above a respective one of the wells 14 when the well plates 12 are properly positioned. Restated, each individual one of the LED's 30 is coupled, in a one-to-one ratio, with a respective one of the wells 14. Such a one-to-one coupling is promoted by the white light emission of the LED's which eliminates the need to have several different types of non-white LED's shining on each plant tissue sample.

Proper positioning of the well plates 12 is ensured by the register depression 26 which urges its respective plate into a predetermined position on one of the shelves 23. For instance, the 4 by 6 array of wells 14 of one of the plates 12 in its registered position corresponds to, and is centered under, the 4 by 6 array of LED's 30, as shown in FIGS. 2 and 7. Centering of one LED above each well allows the distance between the LED and tissue at the bottom of the well to be calibrated so as to provide an optimal amount of light beam spread and intensity to promote tissue growth. Preferably, beam spread for each LED is about a 40° cone. The output intensity at full voltage and current is 5.6 Candela (15–16 lumens/watt at 20 mA) with a 20° beam. The color temperature is 6000 to 6500 Kelvin. Optimum spread angle and intensity, however, will vary depending in part upon the type of plant tissue and the desired rate of growth. To achieve such variations, the LED's can be current limited using resistors to reduce output. Output can also be reduced by pulsing, shortening of duty cycles and/or reducing the voltage. An increase in output can be achieved by increasing voltage and pulsing at a shorter duty cycle.

Arrays of LED's 30 corresponding to well plates 12 with standard arrays of 48 and 96 wells could also be used. In another alternative, the array of LED's 40 could be configured to correspond to a non-standard array of wells, such as an array of 3 or 1000 irregularly spaced wells in a well plate. In yet another alternative, the array of LED's 30 could correspond to several of the well plates 12 disposed on one of the shelves 23. As an example, three of the 4 by 6 well plates 12 could be supported in registered positions on a single one of the shelves 23 and the array of LED's 30 positioned thereabove is a 12 by 6 array.

In an example of the high-density stacking well plates 12 in the rack 20, the low heat and small size of the LED's 30 allow the shelves 23 to be vertically stacked two inches apart. A shelf size of 96 inches by 19 inches would hold 90 standard 4 by 6 well plates 12 and at least 40 shelves stacked vertically in 8 feet of vertical space (a typical storage room). A total of 3600 plates could then be stored and supplied with light in 101 cubic feet of volume. The number of tissue samples for such a configuration would be 86,400. In comparison, 505 cubic feet would be required for the same number of samples when using fluorescent lighting with shelves spaced 1 foot apart and the same 4 by 6 well plates. Further, the low power requirements of the LED's 30 reduce the power required to light each plate from 4.4 watts for fluorescent lights to 1.3 watts with the LED's. The lower power requirements are due in part to the positioning of the LED's with respect to the wells 14 which promotes the efficient distribution of the light from the LED's. In other words, more of the light generated by the LED's reaches the tissue than in fluorescent lighting systems, requiring less light to be generated overall.

During use of the high-throughput screening system 10, circuit boards 31 containing arrays of LED's 30 are selected so as to correspond to the arrays of wells 14 of the plates 12 used in the screening operation. The circuit boards 31 are each attached to a respective one of the card edge connectors 24 by inserting the circuit board into the horizontal slot of the respective connector. Such insertion electrically couples the top and bottom contact areas on the board with the tabs 33 allowing power to be supplied through the power leads 32. Once the boards 31 are energized, the LED's 30 are switched on and begin supplying light.

The tissue samples 13 are loaded into the well plates 12 and fresh liquid media is injected into the wells, preferably using an automated system such as a GENESIS liquid handler manufactured by TECAN of Mannedorf, Switzerland. The well plates 12 containing the fresh plant tissue samples 13 are gripped and positioned by the robot 11's manipulator on the shelves 23 of the rack 20. As each of the well plates 12 is positioned on its respective one of the shelves 23, the register depression 26 urges the well plate into a centered position below the corresponding array of LED's 30. At intervals necessary for the screening process, such as the need to replenish liquid nutrients, sample the liquid of one of the wells, remove some of the tissue samples from the wells or replace one plate with another, the robotic system 11 accesses the appropriate location on one of the shelves 23 and retrieves the plate from its position on the register depression 26.

The present invention has several advantages. The use of LED's 30 that are less bulky and emit less heat than fluorescent and incandescent bulbs allows the shelves 23 of the rack 20 to be more closely stacked. More closely stacked shelves increases storage efficiency by reducing the amount of spaced need to house an adequate supply of tissue samples 13. This is particularly important in high-throughput screening operations where thousands of samples are needed on a daily basis. In addition, more plates are accessible to automated plate manipulators, such as robotic arms, that have a limited range of motion. Matching and alignment of each of the wells 14 with its own light-emitting diode allows for calibration of the light beam spread and intensity for optimal tissue growth. Further, the light emitting diodes 30 have lower power requirements than fluorescent and incandescent bulbs, averaging about 1.3 watts per standard 4 by 6 plate compared to 4.4 watts for fluorescent and incandescent systems. White light emitting LED's 30 have the advantage of emitting a full spectrum of frequencies and therefore being useable for many different types of plant tissue. In addition, the use of white LED's promotes the one-to-one coupling of each LED with its own cell well.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. An assembly for promoting growth of tissue samples requiring light to support proliferation, said assembly comprising:
   a plurality of plates, each of the plates defining therein a plurality of wells arranged in a well array, each of the plurality of wells configured to support and isolate one of the tissue samples;
   a rack including a plurality of supports spaced from each other and configured to support at least one of the plates;
   a plurality of light-emitting diode arrays supported by the rack and cooperating respectively with the supports so that light from the light-emitting diode array shines into the wells of the plate and promotes growth of the tissue samples contained therein; and
   a robotic system configured to automatically load the tissue samples into each of the plurality of wells in the plurality of plates and to position each of the plurality of plates on one of the plurality of supports opposite one of the plurality of light-emitting diode arrays and to remove each of the plurality of well plates from one of the plurality of supports for additional downstream processing.

2. An assembly of claim 1, wherein each of the supports include a register device which urges the plate supported thereon into a register position such that each of the light emitting diodes is centered opposite its respective one of the wells.

3. An assembly of claim 2, wherein the support comprises a shelf and the register device is a register depression defined in the shelf.

4. An assembly of claim 2, wherein the register device is selected from the group consisting of:
   photo-optic sensors;
   mechanical stops; or
   magnetic registers.

5. An assembly of claim 1, wherein the rack further comprises a volume, measured in cubic feet defined by a length, a width, and a height of the rack such that the rack supports the plurality of plates in a high-density arrangement such that the rack contains at least about 288 wells per cubic foot.

6. An assembly of claim 1, wherein each of the plurality of light-emitting diode arrays emits a full spectrum of light frequencies.

7. An assembly for promoting growth of tissue samples requiring light to support proliferation, said assembly comprising:
   a plurality of plates, each of the plates defining therein a plurality of wells arranged in a well array, each of the plurality of wells configured to support and isolate one of the tissue samples;
   a rack including a plurality of supports spaced from each other and configured to support at least one of the plates;
   a plurality of light-emitting diode arrays supported by the rack and cooperating respectively with the supports so that light from the light-emitting diode array shines into the wells of the plate and promotes growth of the tissue samples contained therein, wherein each of the light-emitting diode arrays comprises a plurality of light-emitting diodes arranged in an array corresponding to the well array of the plate such that each of the light emitting diodes is positioned opposite a respective one of the wells; and
   a robotic system configured to automatically load the tissue samples into each of the plurality of wells in the plurality of plates and to position each of the plurality of plates on one of the plurality of supports opposite one of the plurality of light-emitting diode arrays and to remove each of the plurality of well plates from one of the plurality of supports for additional downstream processing.

8. An assembly of claim 7, wherein each of the supports include a register device which urges the plate supported thereon into a register position such that each of the light emitting diodes is centered opposite its respective one of the wells.

9. An assembly of claim 8, wherein the support comprises a shelf and the register device is a register depression defined in the shelf.

10. An assembly of claim 8, wherein the register device is selected from the group consisting of:
    photo-optic sensors;
    mechanical stops; or
    magnetic registers.

11. An assembly of claim 7, wherein the rack further comprises a volume, measured in cubic feet defined by a length, a width, and a height of the rack such that the rack supports the plurality of plates in a high-density arrangement such that the rack contains at least about 288 wells per cubic foot.

12. An assembly of claim 7, wherein each of the plurality of light-emitting diodes emits a full spectrum of light frequencies.

13. An assembly for housing a plurality of plates and supplying light to a plurality of tissue samples, each of the plates defining therein a plurality of wells arranged in a well array, each of the plurality of wells supporting one of the tissue samples, said assembly comprising:
    a rack including a plurality of supports spaced from each other;
    a plurality of light-emitting diode arrays each including a plurality of light-emitting diodes arranged in an array corresponding to the well array wherein each of the light-emitting diode arrays is supported by the rack opposite a respective one of the shelves so that light from each of the light-emitting diodes shines into a respective one of the wells of the plate supported on the shelf; and a robotic system configured to load each of the plurality of wells with one of the plurality of tissue samples, and to position each of the plurality of plates in one of the plurality of supports, and to remove each of the plurality of plates from one of the plurality of supports for additional downstream processing.

14. An assembly of claim 13, wherein each of the shelves is configured to urge at least one of the plurality of plates into a register position.

15. An assembly of claim 13, wherein each of the shelves defines a register depression shaped to urge the plate into a register position.

16. An assembly of claim 13, wherein the rack further comprises a volume, measured in cubic feet defined by a length, a width, and a height of the rack such that the rack supports the plurality of plates in a high-density arrangement such that the rack contains at least about 288 wells per cubic foot.

17. An assembly of claim 13, wherein each of the plurality of light-emitting diodes emits a full spectrum of light frequencies.

18. An assembly for promoting growth of tissue samples requiring light to support proliferation, said assembly comprising:

a plurality of plates, each of the plates defining therein a plurality of wells arranged in a well array, each of the plurality of wells configured to support and isolate one of the tissue samples;

a rack including a plurality of supports spaced from each other and configured to support at least one of the plates;

a plurality of light-emitting diode arrays supported by the rack and cooperating respectively with the supports so that light from the light-emitting diode array shines into the wells of the plate and promotes growth of the tissue samples contained therein, wherein each of the light-emitting diode arrays includes a circuit board and a plurality of light-emitting diodes carried by the circuit board and wherein the rack further includes a plurality of card edge connectors each configured to receive the circuit board of one of the light-emitting diode arrays and support the circuit board and light-emitting diodes above the respective one of the shelves; and a robotic system configured to load each of the plurality of wells with one of the plurality of tissue samples, and to position each of the plurality of plates in one of the plurality of supports, and to remove each of the plurality of plates from one of the plurality of supports for additional downstream processing.

19. An assembly of claim 18, wherein the rack further comprises a volume, measured in cubic feet defined by a length, a width, and a height of the rack such that the rack supports the plurality of plates in a high-density arrangement such that the rack contains at least about 288 wells per cubic foot.

20. An assembly of claim 18, wherein each of the plurality of light-emitting diodes emits a full spectrum of light frequencies.

* * * * *